United States Patent
Swift

(10) Patent No.: US 10,420,538 B2
(45) Date of Patent: Sep. 24, 2019

(54) ILLUMINATED SURGICAL RETRACTOR

(71) Applicant: OBP MEDICAL CORPORATION, Lawrence, MA (US)

(72) Inventor: Jeffrey Ralph Swift, Boca Grande, FL (US)

(73) Assignee: OBP Medical Corporation, Lawrence, MA (US)

( * ) Notice: Subject to any disclaimer, the term of this patent is extended or adjusted under 35 U.S.C. 154(b) by 76 days.

(21) Appl. No.: 15/178,675

(22) Filed: Jun. 10, 2016

(65) Prior Publication Data

US 2016/0310120 A1    Oct. 27, 2016

Related U.S. Application Data

(63) Continuation-in-part of application No. 14/614,413, filed on Feb. 5, 2015, now Pat. No. 9,867,602.

(51) Int. Cl.
*A61B 17/02* (2006.01)
*A61B 90/30* (2016.01)
(Continued)

(52) U.S. Cl.
CPC .............. *A61B 17/02* (2013.01); *A61B 90/30* (2016.02); *A61B 1/0669* (2013.01); *A61B 1/0684* (2013.01); *A61B 1/32* (2013.01); *A61B 2017/0023* (2013.01); *A61B 2017/0092* (2013.01); *A61B 2017/00734* (2013.01);
(Continued)

(58) Field of Classification Search
CPC ..... A61B 17/02; A61B 17/206; A61B 17/218; A61B 17/32; A61B 1/32; A61B 2017/0023; A61B 2017/00734
See application file for complete search history.

(56) References Cited

U.S. PATENT DOCUMENTS

| 559,122 A | 4/1896 | Daily |
| 2,235,979 A | 3/1941 | Brown |

(Continued)

FOREIGN PATENT DOCUMENTS

| CN | 2239235 Y | 11/1996 |
| CN | 2265156 Y | 10/1997 |

(Continued)

OTHER PUBLICATIONS

MakeItFrom.com, https://www.makeitfrom.com/material-properties/Polyetheretherketone-PEEKm, PEEK property table, accessed Sep. 4, 2018, copyright 2009-18.*

(Continued)

*Primary Examiner* — Ellen C Hammond
*Assistant Examiner* — Tessa M Matthews
(74) *Attorney, Agent, or Firm* — Cowan, Liebowitz & Latman, P.C.

(57) ABSTRACT

An illuminated surgical retractor embodiment includes a blade, a handle, a curved section and an illumination assembly. The blade has a top surface and a bottom surface. The handle extends at an angle from a proximal end of the blade. The curved section connects the handle to the blade. The illumination assembly includes at least one light source, at least one battery and an activation device for energizing the light source. In an embodiment, the blade, handle, and curved section are molded from a glass-fiber reinforced polymer.

26 Claims, 10 Drawing Sheets

(51) Int. Cl.
- *A61B 17/00* (2006.01)
- *A61B 1/06* (2006.01)
- *A61B 1/32* (2006.01)

(52) U.S. Cl.
CPC .............. *A61B 2017/00964* (2013.01); *A61B 2090/309* (2016.02)

(56) References Cited

U.S. PATENT DOCUMENTS

| | | |
|---|---|---|
| 2,247,258 A | 6/1941 | Shepard |
| 2,482,971 A | 9/1949 | Golson |
| 2,592,190 A | 4/1952 | Rubens et al. |
| 3,324,850 A | 6/1967 | Gunning |
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |
| 3,638,644 A | 2/1972 | Reick |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitmas |
| 3,815,585 A | 6/1974 | Fiore |
| 3,826,248 A | 7/1974 | Gobels |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collns |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie |
| 5,499,964 A | 3/1996 | Beck et al. |
| 5,512,038 A | 4/1996 | O'Neal et al. |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Shuchman et al. |
| 5,888,195 A | 3/1999 | Schneider |
| 5,899,854 A | 5/1999 | Slishman |
| 5,916,150 A | 6/1999 | Sillman |
| 6,004,265 A | 12/1999 | Hsu |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,217,512 B1 | 4/2001 | Salo |
| 6,231,505 B1 | 5/2001 | Martin |
| 6,254,247 B1 | 7/2001 | Carson |
| 6,277,067 B1 | 8/2001 | Blair |
| 6,319,199 B1 | 11/2001 | Sheehan |
| 6,346,085 B1 | 2/2002 | Schiffman |
| 6,359,644 B1 | 3/2002 | Salvati |
| 6,361,489 B1 | 3/2002 | Tsai |
| 6,379,296 B1 | 4/2002 | Baggett |
| 6,379,299 B1 | 4/2002 | Borodulin |
| 6,394,111 B1 | 5/2002 | Jacobs |
| 6,394,950 B1 | 5/2002 | Weiss |
| 6,416,465 B2 | 7/2002 | Brau |
| 6,428,180 B1 | 8/2002 | Karram et al. |
| 6,432,045 B2 | 8/2002 | Lemperle |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller |
| 6,487,440 B2 | 11/2002 | Deckert |
| 6,504,985 B2 | 1/2003 | Parker et al. |
| 6,523,973 B2 | 2/2003 | Galli |
| 6,524,259 B2 | 2/2003 | Baxter-Jones |
| 6,569,091 B2 | 5/2003 | Diokno |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B1 | 5/2005 | Vail, III |
| 7,014,340 B2 | 3/2006 | Bettis |
| 7,029,439 B2 | 4/2006 | Roberts |
| D520,464 S | 5/2006 | Strong |
| 7,223,223 B2 | 5/2007 | Lindsay |
| 7,276,025 B2 | 10/2007 | Roberts |
| 7,306,559 B2 | 12/2007 | Williams |
| 7,631,981 B2 | 12/2009 | Miller |
| 7,736,304 B2 | 6/2010 | Pecherer |
| 7,758,203 B2 | 7/2010 | McMahon et al. |
| 7,878,973 B2 | 2/2011 | Yee et al. |
| 7,909,759 B2 | 3/2011 | Pecherer |
| 7,967,809 B2 | 6/2011 | Jay-Robinson |
| 8,012,089 B2 | 9/2011 | Bayat |
| 8,047,987 B2 | 11/2011 | Grey et al. |
| 8,088,066 B2 | 1/2012 | Grey et al. |
| 8,096,945 B2 | 1/2012 | Buchok |
| 8,142,352 B2 | 3/2012 | Vivenzio et al. |
| 8,142,353 B2 | 3/2012 | Pecherer et al. |
| 8,157,728 B2 | 4/2012 | Danna et al. |
| 8,162,826 B2 | 4/2012 | Pecherer et al. |
| 8,251,898 B2 | 8/2012 | Pecherer |
| 8,317,693 B2 | 11/2012 | Grey et al. |
| 8,388,523 B2 | 3/2013 | Vivenzio et al. |
| 8,394,017 B2 | 3/2013 | Kieffer |
| 8,435,175 B2 | 5/2013 | McMahon et al. |
| 8,512,234 B2 | 8/2013 | Grey et al. |
| 8,512,237 B2 | 8/2013 | Bastia |

(56) References Cited

U.S. PATENT DOCUMENTS

| | | |
|---|---|---|
| 8,555,892 B2 | 10/2013 | Traub |
| 8,596,847 B2 | 12/2013 | Vayser et al. |
| 8,628,879 B2 | 1/2014 | Pecherer et al. |
| 8,821,385 B2 | 9/2014 | Naito |
| D719,652 S | 12/2014 | Swift |
| 8,979,745 B2 | 3/2015 | Swift |
| 9,050,048 B2 | 6/2015 | Nadershahi et al. |
| D745,669 S | 12/2015 | Swift |
| D752,217 S | 3/2016 | Swift |
| D753,295 S | 4/2016 | Vivenzio et al. |
| 9,307,897 B2 | 4/2016 | Swift |
| 9,332,898 B2 | 5/2016 | McMahon et al. |
| 9,532,706 B2 | 1/2017 | McMahon et al. |
| 9,629,529 B1 | 4/2017 | Indovina et al. |
| 9,718,130 B1 | 8/2017 | Vayser et al. |
| 9,763,743 B2 | 9/2017 | Lin et al. |
| 9,808,231 B2 | 11/2017 | Miraki et al. |
| 9,814,377 B2 | 11/2017 | Lia et al. |
| 9,820,638 B2 | 11/2017 | Cheng |
| 9,820,729 B2 | 11/2017 | Miles et al. |
| 9,826,892 B2 | 11/2017 | Dresher et al. |
| 9,833,295 B2 | 12/2017 | Vayser et al. |
| 9,844,364 B2 | 12/2017 | Grey et al. |
| 9,861,349 B2 | 1/2018 | Nadershahi et al. |
| 9,867,531 B2 | 1/2018 | Pacey et al. |
| 9,877,639 B2 | 1/2018 | Grey et al. |
| 9,877,644 B2 | 1/2018 | Greenstein et al. |
| D809,660 S | 2/2018 | Nguyen et al. |
| 9,883,792 B2 | 2/2018 | McMahon et al. |
| 9,888,957 B2 | 2/2018 | Wolf et al. |
| 9,907,544 B2 | 3/2018 | Nadershahi et al. |
| 9,913,682 B2 | 3/2018 | Wolf et al. |
| 9,918,618 B2 | 3/2018 | Molnar |
| 9,918,802 B2 | 3/2018 | Coppersmith et al. |
| 9,931,028 B2 | 4/2018 | Lia et al. |
| 9,943,295 B2 | 4/2018 | King |
| 9,949,814 B2 | 4/2018 | Alexander et al. |
| 9,955,858 B2 | 5/2018 | Pamnani et al. |
| 9,968,262 B2 | 5/2018 | Greenstein et al. |
| 9,968,346 B2 | 5/2018 | Alexander et al. |
| 9,980,710 B2 | 5/2018 | Seifert et al. |
| 9,986,901 B2 | 6/2018 | Grey et al. |
| 9,986,903 B2 | 6/2018 | Nadershahi et al. |
| 9,986,988 B2 | 6/2018 | Ferro et al. |
| 9,999,345 B2 | 6/2018 | Vayser et al. |
| 10,004,392 B2 | 6/2018 | Millard et al. |
| 10,004,393 B2 | 6/2018 | Kucklick |
| 10,028,648 B2 | 7/2018 | Goldfain et al. |
| 10,028,649 B2 | 7/2018 | Salvati et al. |
| 10,028,780 B2 | 7/2018 | Wolf et al. |
| 10,045,686 B2 | 8/2018 | Ou Yang et al. |
| 10,045,731 B2 | 8/2018 | Prasad et al. |
| 10,052,432 B2 | 8/2018 | Dexter et al. |
| 10,064,611 B2 | 9/2018 | Ross et al. |
| 10,064,613 B2 | 9/2018 | Davis et al. |
| 10,068,173 B2 | 9/2018 | Vayser et al. |
| 10,092,176 B2 | 10/2018 | Kienzle et al. |
| 10,092,281 B2 | 10/2018 | Perler et al. |
| 10,098,530 B2 | 10/2018 | McMahon et al. |
| 10,105,043 B2 | 10/2018 | George |
| 10,117,646 B2 | 11/2018 | Friedrich et al. |
| 10,130,441 B2 | 11/2018 | Martinez |
| 10,166,016 B2 | 1/2019 | Shimizu et al. |
| 10,172,601 B2 | 1/2019 | Ann |
| 10,174,933 B2 | 1/2019 | Phillips, Jr. et al. |
| 10,188,298 B2 | 1/2019 | Greenstein et al. |
| 10,213,271 B2 | 2/2019 | Duggal et al. |
| 10,219,800 B2 | 3/2019 | Tsubouchi |
| 10,220,445 B2 | 3/2019 | Vayser et al. |
| 10,226,555 B2 | 3/2019 | Vayser et al. |
| 10,238,462 B2 | 3/2019 | Wood et al. |
| D846,119 S | 4/2019 | Greeley et al. |
| 10,278,571 B2 | 5/2019 | Poormand |
| 10,292,782 B2 | 5/2019 | Haverich et al. |
| 10,292,784 B2 | 5/2019 | Duggal et al. |
| 2001/0029044 A1 | 10/2001 | Gombrich |
| 2002/0022769 A1 | 2/2002 | Smith |
| 2002/0038075 A1 | 3/2002 | Tsai |
| 2002/0038076 A1 | 3/2002 | Sheehan |
| 2002/0055670 A1 | 5/2002 | Weiss |
| 2002/0156350 A1 | 10/2002 | Nieto |
| 2002/0165435 A1 | 11/2002 | Weiss |
| 2002/0198471 A1 | 12/2002 | Baxter-Jones |
| 2003/0095781 A1 | 5/2003 | Willaims |
| 2003/0139673 A1 | 7/2003 | Vivenzio |
| 2003/0158502 A1 | 8/2003 | Baxter-Jones |
| 2003/0176772 A1 | 9/2003 | Yang |
| 2003/0187331 A1 | 10/2003 | Faludi |
| 2004/0026829 A1 | 2/2004 | Van Der Weegen |
| 2004/0054260 A1 | 3/2004 | Klaassen et al. |
| 2004/0141175 A1 | 7/2004 | Baldwin |
| 2004/0183482 A1 | 9/2004 | Roberts |
| 2004/0184288 A1 | 9/2004 | Bettis |
| 2004/0186355 A1 | 9/2004 | Strong |
| 2005/0065496 A1 | 3/2005 | Simon |
| 2005/0085699 A1 | 4/2005 | Weiss |
| 2005/0085723 A1 | 4/2005 | Huebner |
| 2005/0159649 A1 | 7/2005 | Patel |
| 2005/0192482 A1 | 9/2005 | Carpenter |
| 2005/0215858 A1 | 9/2005 | Vail, III |
| 2005/0240081 A1 | 10/2005 | Eliachar |
| 2005/0277811 A1 | 12/2005 | Richards et al. |
| 2006/0084843 A1 | 4/2006 | Sommerich |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0100212 A1 | 5/2007 | Pimenta et al. |
| 2007/0208226 A1* | 9/2007 | Grey ............... A61B 17/02 600/212 |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2007/0293729 A1* | 12/2007 | Grey ............... A61B 1/00105 600/212 |
| 2008/0002426 A1 | 1/2008 | Vayser et al. |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |
| 2008/0319290 A1* | 12/2008 | Mao ............... A61B 5/0086 600/323 |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0275603 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1* | 2/2010 | Bonnadier ......... A61B 17/1659 606/85 |
| 2010/0041955 A1 | 2/2010 | Grey et al. |
| 2010/0191062 A1 | 7/2010 | Kieffer |
| 2010/0292533 A1 | 11/2010 | Kasahara et al. |
| 2011/0022032 A1 | 1/2011 | Zemlok et al. |
| 2012/0055470 A1 | 3/2012 | Pecherer et al. |
| 2012/0059226 A1 | 3/2012 | Funt |
| 2012/0078060 A1 | 3/2012 | Swift |
| 2012/0116170 A1 | 5/2012 | Vayser et al. |
| 2013/0018230 A1 | 1/2013 | Su et al. |
| 2013/0041229 A2 | 2/2013 | Hahn et al. |
| 2013/0197313 A1* | 8/2013 | Wan ............... A61B 1/32 600/202 |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |
| 2014/0088371 A1 | 3/2014 | Vayser et al. |
| 2014/0179998 A1* | 6/2014 | Pacey ............... A61B 17/02 600/103 |
| 2014/0202459 A1 | 7/2014 | Iqbal |

(56) References Cited

U.S. PATENT DOCUMENTS

| | | |
|---|---|---|
| 2014/0275790 A1 | 9/2014 | Vivenzio |
| 2014/0309499 A1 | 10/2014 | Swift |
| 2014/0316211 A1 | 10/2014 | Hermle |
| 2014/0323800 A1 | 10/2014 | Dye |
| 2014/0364695 A1 | 12/2014 | Nadershahi et al. |
| 2014/0371536 A1 | 12/2014 | Miller et al. |
| 2015/0018625 A1 | 1/2015 | Miraki et al. |
| 2015/0157469 A1 | 6/2015 | Prado et al. |
| 2015/0238070 A1 | 8/2015 | Lia et al. |
| 2015/0285382 A1 | 10/2015 | Kienreich et al. |
| 2016/0000305 A1 | 1/2016 | Elbaz et al. |
| 2016/0038032 A1 | 2/2016 | Dan |
| 2016/0051136 A1* | 2/2016 | Lauchner .............. A61B 17/00 600/214 |
| 2016/0095506 A1 | 4/2016 | Dan et al. |
| 2016/0100751 A1 | 4/2016 | Davis et al. |
| 2016/0302657 A1 | 10/2016 | Hussey et al. |
| 2017/0007228 A1 | 1/2017 | Costabile |
| 2017/0020621 A1* | 1/2017 | Huldin .................. A61B 90/39 |
| 2017/0035404 A1* | 2/2017 | Foster .................... A61B 17/02 |
| 2017/0065282 A1 | 3/2017 | Mathis et al. |
| 2017/0079518 A1 | 3/2017 | Elbaz et al. |
| 2017/0172404 A1 | 6/2017 | McMahon et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 6/2017 | Vayser |
| 2017/0300623 A1 | 10/2017 | Rosenblatt et al. |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0036095 A1 | 2/2018 | Vayser et al. |
| 2018/0042596 A1 | 2/2018 | Tsubouchi |
| 2018/0064316 A1 | 3/2018 | Charles et al. |
| 2018/0064317 A1 | 3/2018 | Tesar |
| 2018/0078301 A1 | 3/2018 | Vayser |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0271681 A1 | 9/2018 | Ou Yang et al. |
| 2018/0280011 A1 | 10/2018 | Ferro et al. |
| 2018/0296082 A1 | 10/2018 | Salvati et al. |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2018/0336474 A1 | 11/2018 | Vayser et al. |
| 2018/0344144 A1 | 12/2018 | Bouquet |
| 2018/0353059 A1 | 12/2018 | Tesar |
| 2018/0360301 A1 | 12/2018 | Kucklick |
| 2019/0038273 A1 | 2/2019 | Perler et al. |
| 2019/0049655 A1 | 2/2019 | Zagatsky et al. |
| 2019/0076138 A1 | 3/2019 | Opperman |
| 2019/0083079 A1 | 3/2019 | Shimizu et al. |
| 2019/0133432 A1 | 5/2019 | Tsai |
| 2019/0143006 A1 | 5/2019 | Vayser et al. |
| 2019/0143414 A1 | 5/2019 | Vayser et al. |
| 2019/0150422 A1 | 5/2019 | Welch |
| 2019/0150725 A1 | 5/2019 | Ramanujam et al. |
| 2019/0150739 A1 | 5/2019 | Wawro et al. |
| 2019/0150786 A1 | 5/2019 | Vassallo et al. |
| 2019/0167111 A1 | 6/2019 | Greenstein et al. |
| 2019/0167378 A1 | 6/2019 | Wood et al. |

FOREIGN PATENT DOCUMENTS

| | | |
|---|---|---|
| CN | 2516109 Y | 10/2002 |
| CN | 2629738 Y | 8/2004 |
| CN | 1556664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 102415869 A | 4/2012 |
| CN | 302536685 S | 8/2013 |
| CN | 203591245 U | 5/2014 |
| CN | 103925266 A | 7/2014 |
| CN | 203898367 U | 10/2014 |
| CN | 102573700 B | 12/2014 |
| DE | 2128855 A | 12/1972 |
| DE | 202004002963 U1 | 5/2004 |
| DE | 202005019780 U1 | 5/2006 |
| DE | 600 33 612 T2 | 12/2007 |
| EP | 0190014 A2 | 8/1986 |
| FR | 2490478 A1 | 3/1982 |
| RU | 2187972 C2 | 8/2002 |
| RU | 2308873 C2 | 10/2007 |
| WO | 9825512 A1 | 6/1998 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2009137017 A2 | 11/2009 |
| WO | 2013-044151 A1 | 3/2013 |
| WO | 2014-041172 A1 | 3/2014 |
| WO | 2006121530 A2 | 11/2016 |

OTHER PUBLICATIONS

Solvay, Solvay Specialty Polymers, www.SolvaySpecialyPolymers.com, Technical Data, Ixef 1022 polyarylamide, accessed Sep. 4, 2018, copyright 2011.*

The above foreign patent documents were cited in a Nov. 1, 2017 Chinese Office Action, which is enclosed without an English Translation, that issued in Chinese Patent Application No. 2017102800054450.

U.S. Patent references 1-5 and U.S. Published Patent Application references 2 and 4 were cited in an Office Action issued in U.S. Appl. No. 15/171,571.

U.S. Published Patent Application references 1, 3 and 5 were cited in a PCT Search Report issued in PCT Application No. PCT/US2017/042617.

International Search Report for International application No. PCT/US2016/016154 dated May 19, 2016 for corresponding U.S. Appl. No. 14/614,413.

International Search Report, for International application No. PCT/US2016/035508 dated Sep. 15, 2016 for corresponding U.S. Appl. No. 15/171,581.

International Search Report for International application No. PCT/US2016/036833 dated Jan. 19, 2017.

The above foreign patent document 1 was cited in the Jul. 16, 2018 Chinese Office Action, which is enclosed without an English Translation, that issued in Chinese Patent Application No. 201510543086.7.

The above Foreign Patent documents were cited in a European Search Report dated Nov. 23, 2018, which is enclosed, that issued in the corresponding European Patent Application No. 16747107.7.

The above documents were cited in a European Search Report dated Nov. 23, 2018, which is unclosed, that issued in the corresponding European Patent Application No. 16747107.7.

(56) References Cited

OTHER PUBLICATIONS

The above patent was cited in a Oct. 29, 2018 Chinese Office Action, which is enclosed without an English Translation, that issued in Chinese Patent Application No. 201711159829.6.

The above U.S. Publications documents #1 and #2 were cited in a Supplementary European Search Report dated Apr. 24, 2019, which is enclosed, that issued in European Patent Application No. 16804432.9.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

European Search Report of EP16747107.7, dated Nov. 23, 2018, which is enclosed.

\* cited by examiner

ILLUMINATED SURGICAL RETRACTOR

CROSS-REFERENCE TO RELATED APPLICATIONS

This application is a continuation-in-part of U.S. patent application Ser. No. 14/614,413, filed on Feb. 5, 2015, and entitled "Illuminated Surgical Retractor." The entire contents of that application are incorporated herein by reference.

INTRODUCTION

Existing technology for illumination during surgical/medical procedures includes overhead illumination. This illumination comes from either overhead lighting or head mounted fiber optic systems. Traditional overhead lighting systems face numerous limitations. A direct exposure of the field from the overhead source is required. Changes in patient or surgeon positioning may interfere with the light source. Frequent adjustments provide an inconvenience for the surgeon and disrupt the surgical flow. Overhead lighting is frequently inadequate for surgery in deeper cavities where more intense focused illumination may be required.

In addition, the alignment of the surgeon's head frequently interferes with the remote illumination and prevents light from reaching the field. Head mounted fiber optic systems are used frequently for more limited surgical exposures. However, these devices have numerous limitations.

First, the surgeon is tethered by the light cord attached to the headset, limiting the mobility in the operating room.

Second, the devices are associated with head and neck fatigue with frequent or prolonged use.

Third, the devices require the surgeon to maintain a steady head and neck position to provide a constant and steady illumination of the field.

Fourth, the use of remote light sources and fiber bundles introduces tremendous inefficiencies into the system. A typical ten-foot long cable will lose illumination by approximately 10% per foot of cable for a 300-watt light source, which results in much lower illumination than desired.

Fifth, a head lamp's illumination is not collinear with the doctor's eyes, and may cast shadows in the field of view when illuminating surgical cavities.

Sixth, halogen bulbs get very hot and often burn the skin surrounding the surgical pocket the surgeon is working in.

Other existing technology for illumination during surgical/medical procedures includes lighted surgical retractors. These retractors include integral or attached light sources which project light locally down the retractor blade. Existing lighted surgical retractors overcome the problems with overhead illumination, but still suffer from several shortcomings. These retractors can generally be classified into two categories.

The first category includes those with detachable light sources. This category allows the retractor to be re-used and therefore the retractor must be sterilized prior to re-use. Characteristics of most light sources are not compatible with many sterilization procedures. For example, it is uncommon for batteries to carry out high temperature sterilization. It is also difficult to completely remove organic material from light source assemblies.

To overcome these difficulties, lighted surgical retractors with detachable light sources were created. These light sources are releasably attached to the retractor via tape or other adhesive or clip-on mechanism. This class of lighted surgical retractors requires assembly prior to use and disassembly, cleaning, and sterilization after use. Such assembly, disassembly, cleaning, and sterilization represent significant time, cost, and inefficiency for the user.

The second category of lighted surgical retractors consists of surgical retractors with light sources that are integrated into the retractor and are not removable. These lighted surgical retractors contain a power source in the retractor handle, an illumination device built into, or permanently attached to the blade, and some form of optical or electrical coupling between the power source and the illumination device. The power source can be batteries or a device that will plug into the wall. It could also be an optical power source that generates optical energy instead of electrical energy. The illumination device is either one or more light emitting diodes, filament light bulbs, a fiber optic cable, or an optical waveguide. The form of coupling is either wiring for an electrical connection, or a fiber optic cable or optical waveguide for optical coupling.

This second category of lighted surgical retractors eliminates the problem of assembly and disassembly from which the first category of surgical retractors suffers. But this second class of retractors still suffers from difficulty in cleaning and sterilization.

Moreover, in order to be sterilizable (i.e., to withstand the thermal trauma of high pressure steam sterilization), surgical retractors have been generally made of stainless steel. If they had any attached lighting system this required hand disassembly after use, hand cleaning and then repackaging for gas sterilization of the lighting apparatus. This device then required reassembly on the surgical table prior to use.

Also, the known techniques involved in integrating light source components into the handle and blade are generally costly. Recent evidence is emerging that procedures for cleaning and sterilization are often flawed in practice, resulting in possible cross contamination of patients. These deficiencies have prevented a widespread adoption of this second category of lighted surgical retractors.

Embodiments described herein represent a new class of lighted surgical retractors that does not suffer from these known deficiencies. These embodiments completely eliminate the risk of cross contamination by ensuring that each retractor can be only used once. These embodiments eliminate the costly electrical or optical interconnect systems required by previous retractors. These embodiments also eliminate the requirement of assembly, disassembly, cleaning, and re-sterilization by the end user.

Embodiments described herein provide an illuminated surgical retractor, which can be discarded after a single use due to its intrinsic low cost.

In one or more exemplary embodiments, an illuminated surgical retractor includes a blade, a handle, a curved section, and an illumination assembly. The blade has a top surface and a bottom surface. The handle extends at an angle from a proximal end of the blade. The curved section connects the handle to the blade. The illumination assembly includes at least one light source, at least one battery and an activation device for energizing the light source. The illumination assembly is permanently attachable to the curved section.

In one or more embodiments, a chemical capacity of the battery is sufficient for a single use.

In one or more embodiments, the illumination assembly includes a light case integrally molded.

In one or more embodiments, the illumination assembly includes a plurality of retaining tabs protruded from the light case. The illuminated surgical retractor further includes a plurality of acceptance slots and an acceptance cavity. The acceptance slots are located vertically, horizontally or at an angle with the curved section, and are configured for accepting the retaining tabs. The acceptance cavity is in communication with the acceptance slots. When the retaining tabs are inserted fully into the acceptance slots, the retaining tabs arrive at the acceptance cavity.

When compared with the prior art, the exemplary embodiments described herein have at least the following advantages:

(1) The non-directional shape of the retaining tab allows the illumination assembly to be utilized with either vertically released molds or horizontally released molds. This use of a common illumination assembly for a wide variety of retractor shapes dramatically lowers the cost of the illuminated surgical retractor.

(2) The chemical capacity of the batteries is sufficient for only a single use and the illuminated surgical retractor is discarded after the single use. The intrinsic low cost of these embodiments makes the illuminated surgical retractor economically attractive, and eliminates the inefficiency and expense of cleaning and re-sterilization.

(3) The materials and structure enable the device to be radiolucent, allowing patient imaging devices to directly view the body cavity with the retractor inserted.

(4) The materials and structure enable the device to be electroresistive, allowing the physician to utilize electrocauterizing tools in the cavity while the retractor is inserted without worry of shorting out the electrocauterizing tool.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the retractor; wherein the blade, handle, and curved section are molded from a glass-fiber reinforced polymer.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the retractor; wherein the blade, handle, and curved section are molded from a low conductivity polymer.

One exemplary aspect comprises an illuminated surgical retractor, comprising: a blade having a top surface and a bottom surface; a handle extending at an angle from a proximal end of the blade; a curved section connecting the handle to the blade; and an illumination assembly comprising at least one light source, at least one battery and an activation device for energizing the light source, and the illumination assembly being permanently attached to the curved section; wherein the blade, handle, and curved section are molded from a radiolucent polymer.

In various embodiments: (1) the polymer is a 50% glass-fiber reinforced polymer; (2) the polymer is a polyarylamide compound; (3) the polymer is a thermoplastic crystalline polymer; (4) the polymer is a thermoplastic crystalline polymer of aromatic diamines and aromatic dicarboxylic anhydrides; (5) the polymer is a glass-fiber reinforced polyacrylamide; (6) the polymer is at least 50% glass-fiber reinforced; (7) the polymer has a flexural modulus of at least 17 Gpa; (8) the polymer has a flexural strength of at least 375 Mpa; (9) the polymer has an impact strength of at least 100 J/M; (10) the illumination assembly is permanently attached to the curved portion; and/or (11) the polymer has a conductivity of less than $10-6$ A.

Further features and advantages will be apparent to those skilled in the art after reviewing the drawings and detailed description provided herein.

DETAILED DESCRIPTION OF SELECT EMBODIMENTS

Figure 1:
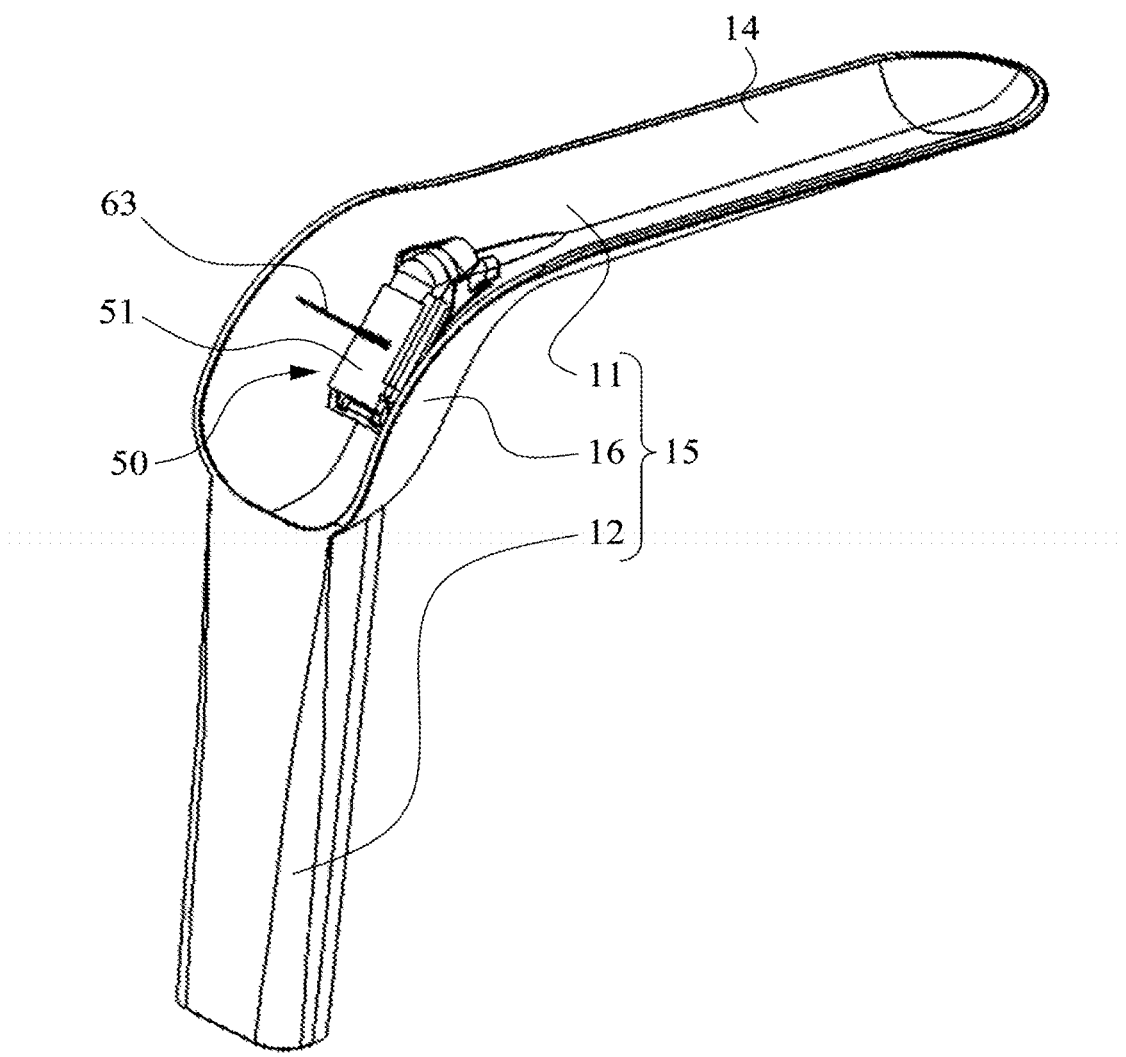
FIG. 1 is a schematic view of an illuminated surgical retractor according to an embodiment of the present disclosure.

Drawings will be used herein to describe select exemplary embodiments. For the sake of clear illustration, many practical details will be explained together in the description below. However, it should be appreciated that the practical details should not be used to limit the claim scope. In other words, in some embodiments, certain details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art. It should be further understood that terms, such as those defined in commonly used dictionaries, should be interpreted as having a meaning that is consistent with their meaning in the context of the relevant art and the present description, and should not be interpreted in an idealized or overly formal sense unless expressly so defined herein.

Figure 2:
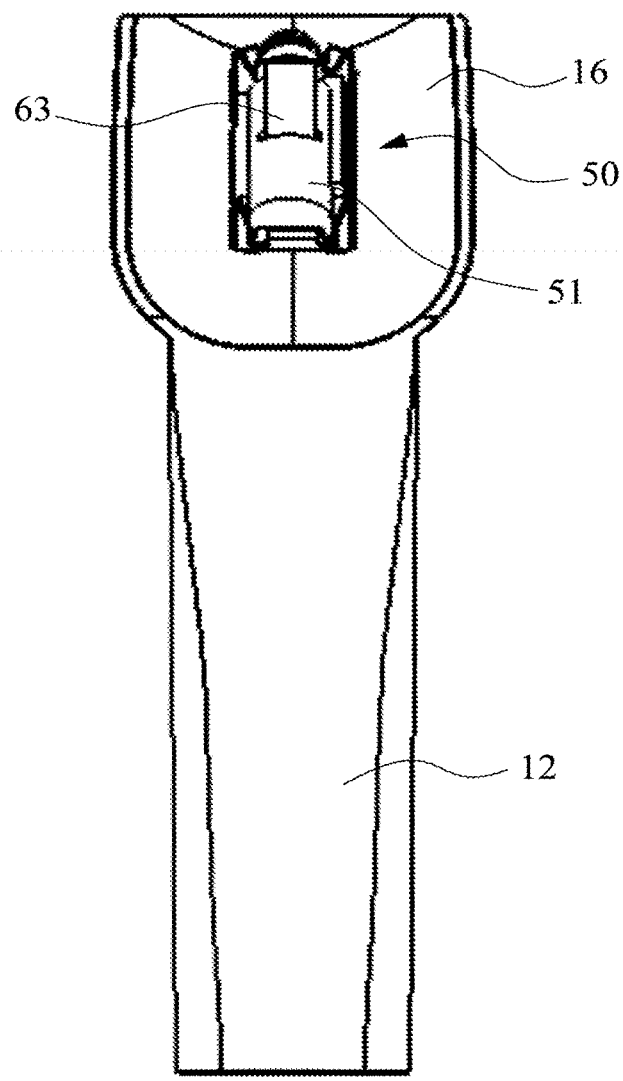
FIG. 2 is a rear view of the illuminated surgical retractor of FIG. 1.

FIG. 1 is a schematic view of an illuminated surgical retractor 10 according to an exemplary embodiment. FIG. 2 is a rear view of the illuminated surgical retractor 10 of FIG. 1. As shown in FIGS. 1-2, an illuminated surgical retractor 10 includes a blade 11, a handle 12, a curved section 16 and an illumination assembly 50. The blade 11 has a top surface 14 and a bottom surface. The handle 12 extends at an angle from a proximal end of the blade 11. The curved section 16 connects the handle 12 to the blade 11. The illumination assembly 50 includes at least one light source 64, at least one battery 62 and an activation device for energizing the light source 64. The illumination assembly 50 is attachable to the curved section 16.

Furthermore, the blade 11 and the handle 12 are joined together at an angle through the curved section 16 to form a retractor component 15. In practical applications, the blade 11, the handle 12, and the curved section 16 are integrally molded as a single piece. In addition, in this embodiment, the angle may be in a range of, for instance, 35 to 170 degrees, and can particularly be 90 degrees. The retractor component 15 may be made of any material, but preferably high strength plastic such as ABS or polyarylamide and made by a low cost manufacturing process such as injection molding. The top surface 14 of the blade 11 may be concave (or flat, or convex).

The blade 11 may have uniform width or may be shaped such that the distal end Is wider or narrower than the proximal end. The blade 11 may have a lip at the end of it for retaining tissue, or may be curved as shown to prevent retention of tissue. In this embodiment, the handle 12 is in a rectangular form, but in other embodiments, the handle 12 may be circular or oval in shape, and may be opened on one or more sides. The illumination assembly 50 is integrated into the angular space connecting the blade 11 with the handle 12. Integration into this angular space allows the batteries 62 and the illumination assembly 50 to reside in a light enclosure 51 and eliminates the electrical or optical coupling requirements in previous disclosures.

Figure 3:
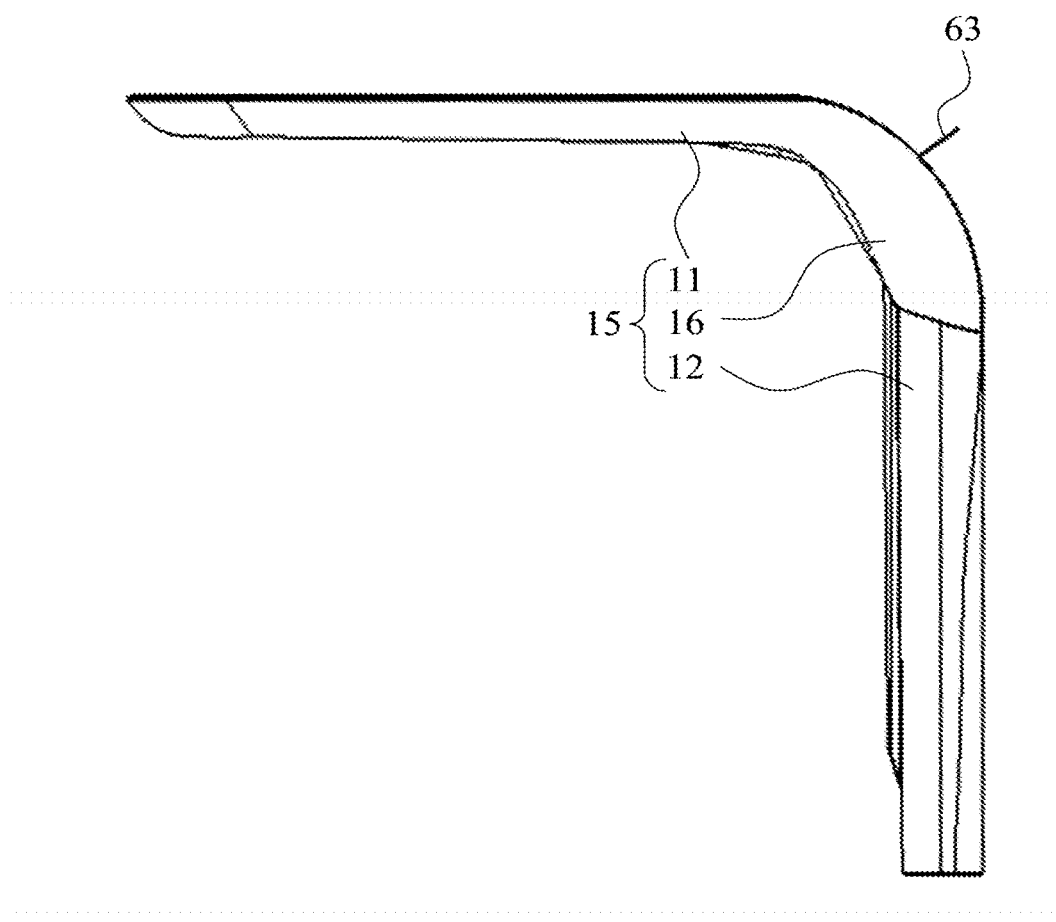
FIG. 3 is a side view of the illuminated surgical retractor of FIG. 1.

FIG. 3 is a side view of the illuminated surgical retractor 10 of FIG. 1. In this embodiment, as shown in FIG. 3, the removal of pull tab 63 is used to energize the illumination assembly 50. Other embodiments may include the use of an electrical switch.

Figure 4:
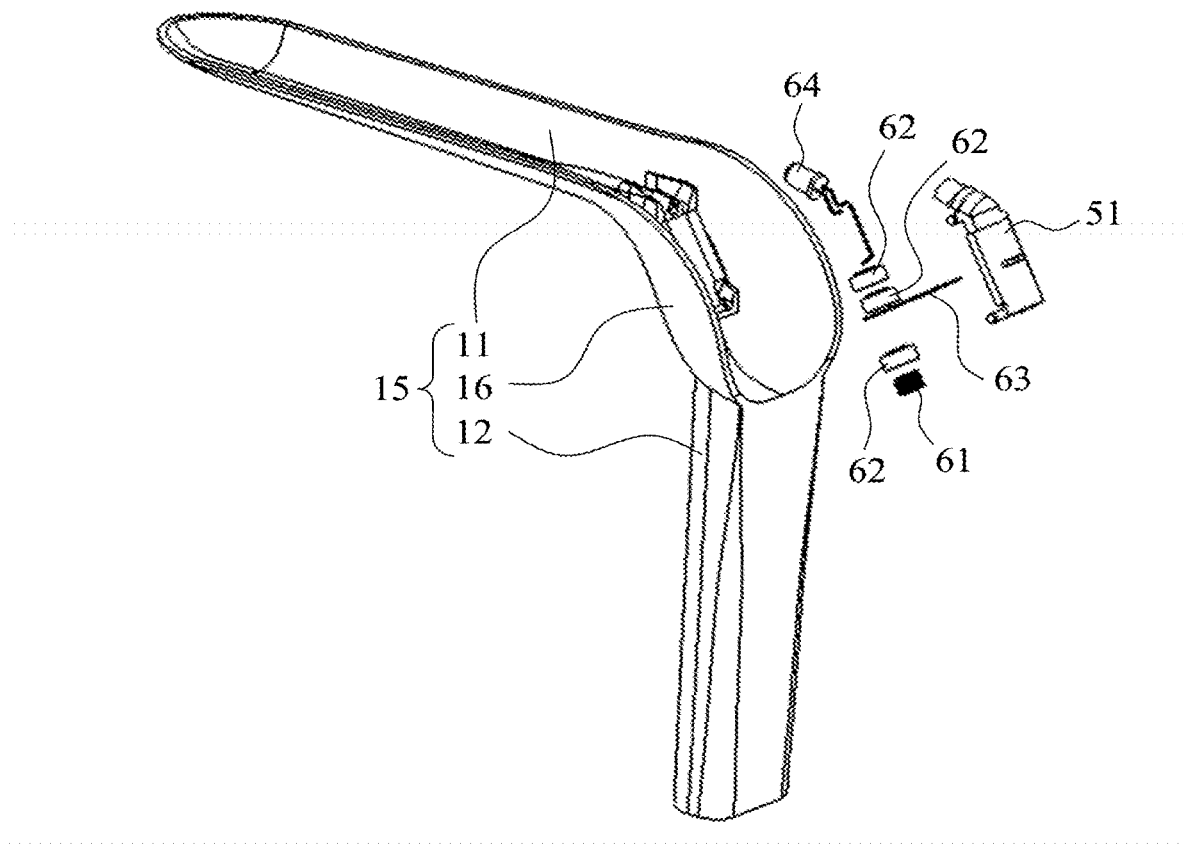
FIG. 4 is an exploded view of the illuminated surgical retractor of FIG. 1.

FIG. 4 is an exploded view of the illuminated surgical retractor 10 of FIG. 1. The light source 64 is used to provide illumination to the area of the blade 11 of the illuminated surgical retractor 10. The light source 64 can be any suitable light source, such as, for example, a light emitting diode (LED), an incandescent element, or a fluorescent element.

In this embodiment, the light source 64 is angled so that substantially all of the light travels to the distal end of the blade 11. In other embodiments, the light source 64 can be angled so as to provide substantially all of the light above the blade 11, or at other angles to the blade 11 that are preferable for the medical application of the illuminated surgical retractor 10.

The batteries 62 provide power to the light source 64. The batteries 62 are small enough to be contained in the angled space between the blade 11 and the handle 12. Examples of the batteries 62 include LR41 or AG3 type button batteries. These batteries 62 are of a very low price. In this embodiment, three batteries 62 are used to provide power to the light source 64. Three batteries 62 eliminate the need for expensive circuitry to condition the voltage and current required by the light source 64. These batteries 62 contain sufficient energy for 20-40 minutes of use, which is sufficient for the vast majority of medical procedures. In other embodiments, a different number and type of batteries 62 can be used with or without conditioning circuitry.

Figure 5:
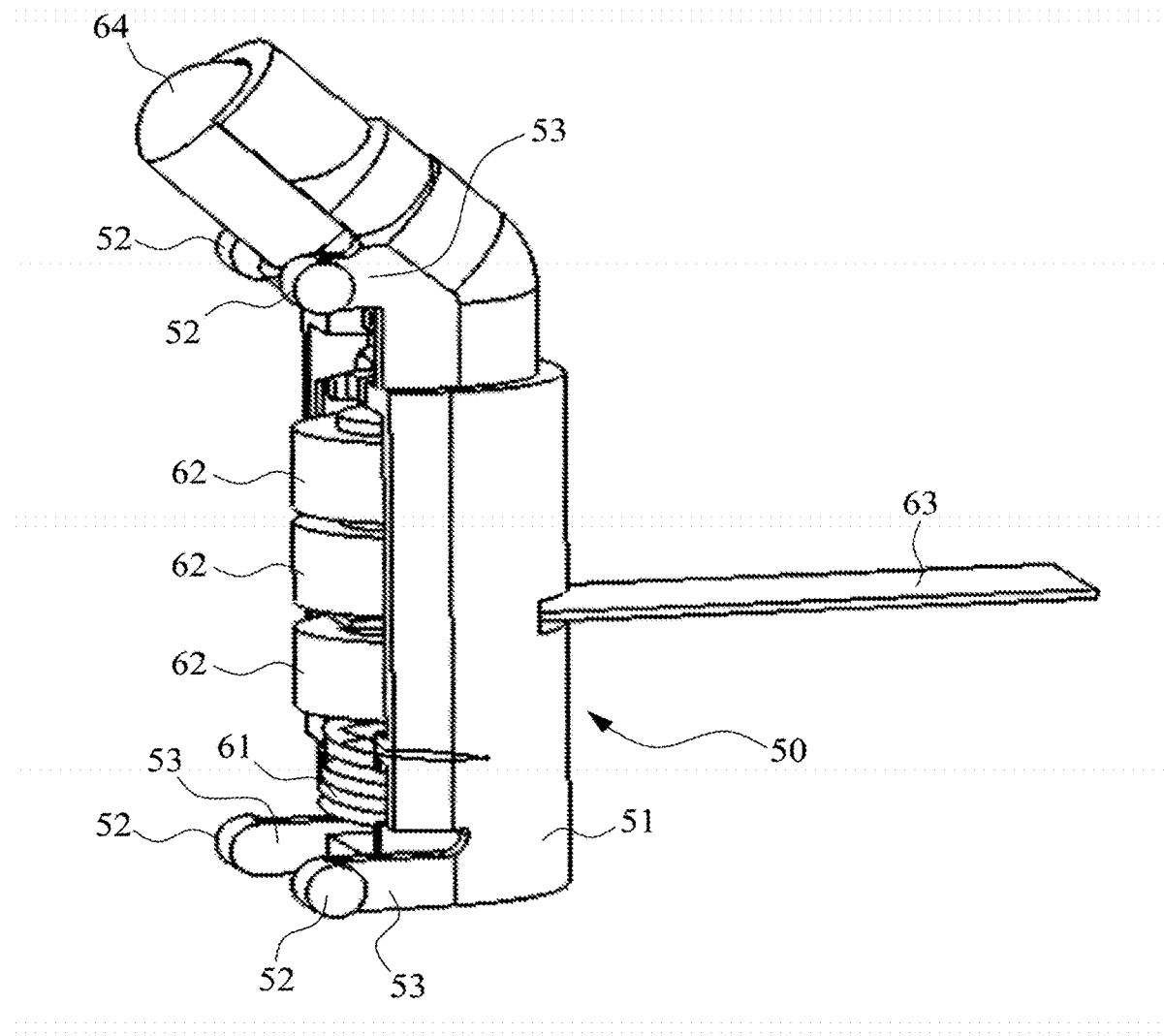
FIG. 5 is a schematic view of the illumination assembly of the illuminated surgical retractor of FIG. 1.
Figure 6:
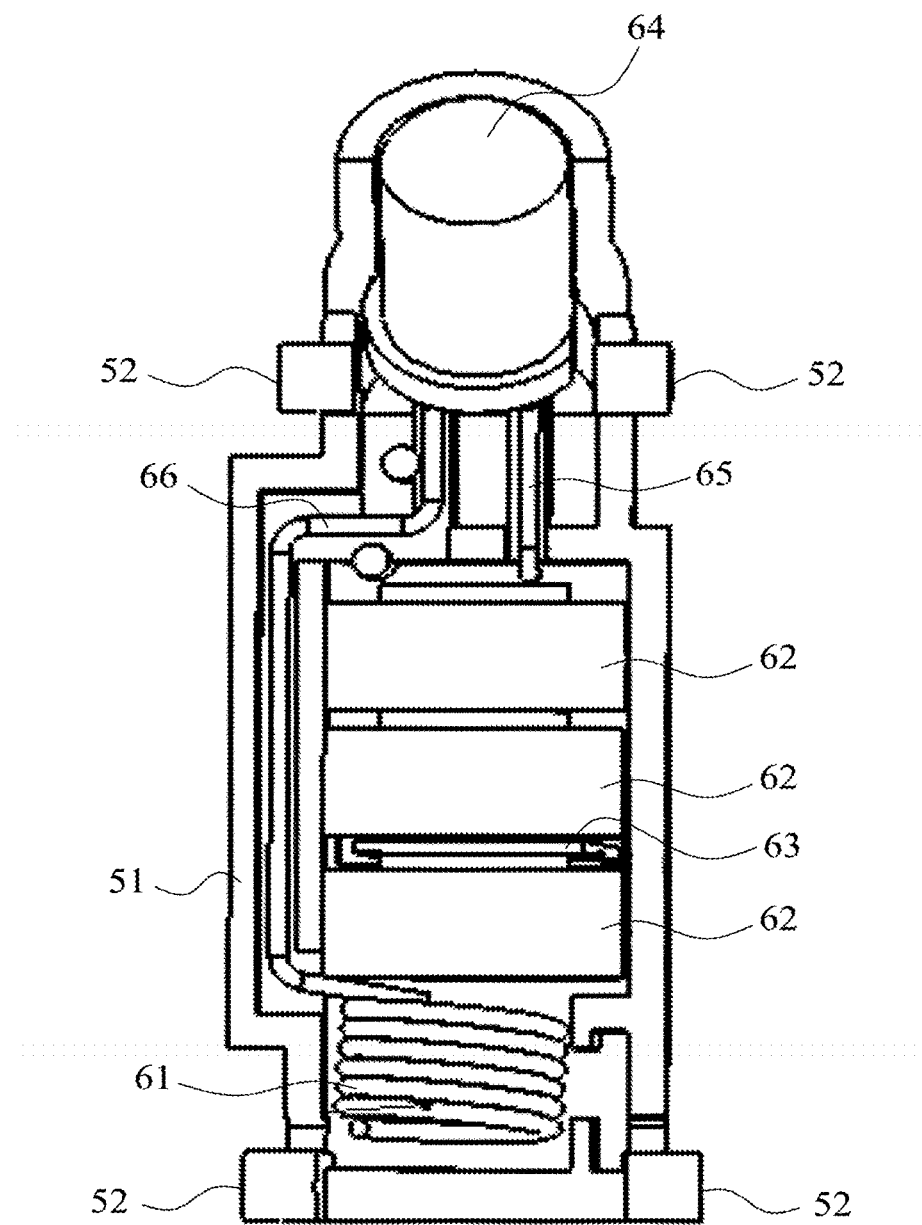
FIG. 6 is a front view of the illumination assembly of FIG. 5.

FIG. 5 is a schematic view of the illumination assembly 50 of the illuminated surgical retractor 10 of FIG. 1. FIG. 6 is a front view of the illumination assembly 50 of FIG. 5. The light case 51 contains the light source 64, the batteries 62, a spring 61, and the pull tab 63. The light source 64 has electrical leads 65 and 66 which are cut to an appropriate length and bent such that the electrical lead 65 makes an electrical contact with the anode or cathode of one battery 62 and the electrical lead 66 makes an electrical contact with the spring 61. In this embodiment, the spring 61 is made of a metal such as stainless steel. In other embodiments, other electrically conductive materials suitable for producing a spring may be used. The spring 61 makes an electrical contact with the opposite battery polarity other than that previously mentioned, and the spring 61 makes this contact with one battery 62.

The spring 61 is assembled in a compressed condition such that the spring 62 applies a force to the batteries 62, the pull tab 63, and the light source leads 65 and 66. This force ensures electrical contact between the batteries 62, the light source leads 65 and 66, the spring 61, and the pull tab 63. The pull tab 63 is made of an electrically insulative material such as polymer, plastic, or film. The pull tab 63 prevents an electric current from flowing to the light source 64 while the pull tab 63 is inserted between two of the batteries 62. The removal of the pull tab 63 will cause the spring 61 to push together the batteries 62 and allow an electric current to flow to the light source 64. Thus, light is emitted from the light source 64. The application of the pull tab 63 is a very low cost method to control the energizing of the electrical circuit. In other embodiments, a switch may be utilized instead of the pull tab 63 to complete the circuit of the batteries 62 and the light source 64. One having ordinary skill in the art will understand these other embodiments.

As shown in FIGS. 5-6, the illumination assembly 50 includes a light case 51. Retaining tabs 52 protrude from the light case 51. The light case 51 is integrally molded and in this embodiment is made of a moldable material such as plastic or nylon, although in other embodiments other materials may be used. Moreover, the illumination assembly 50 includes a plurality of retaining tabs 52. To be more specific, the retaining tabs 52 are located at the distal end of the legs 53, and are protruded at right angles to the legs 53. In this embodiment, the retaining tabs 52 are initially compressed when inserted into acceptance slots 71 (not shown in FIGS. 5-6).

Figure 7:
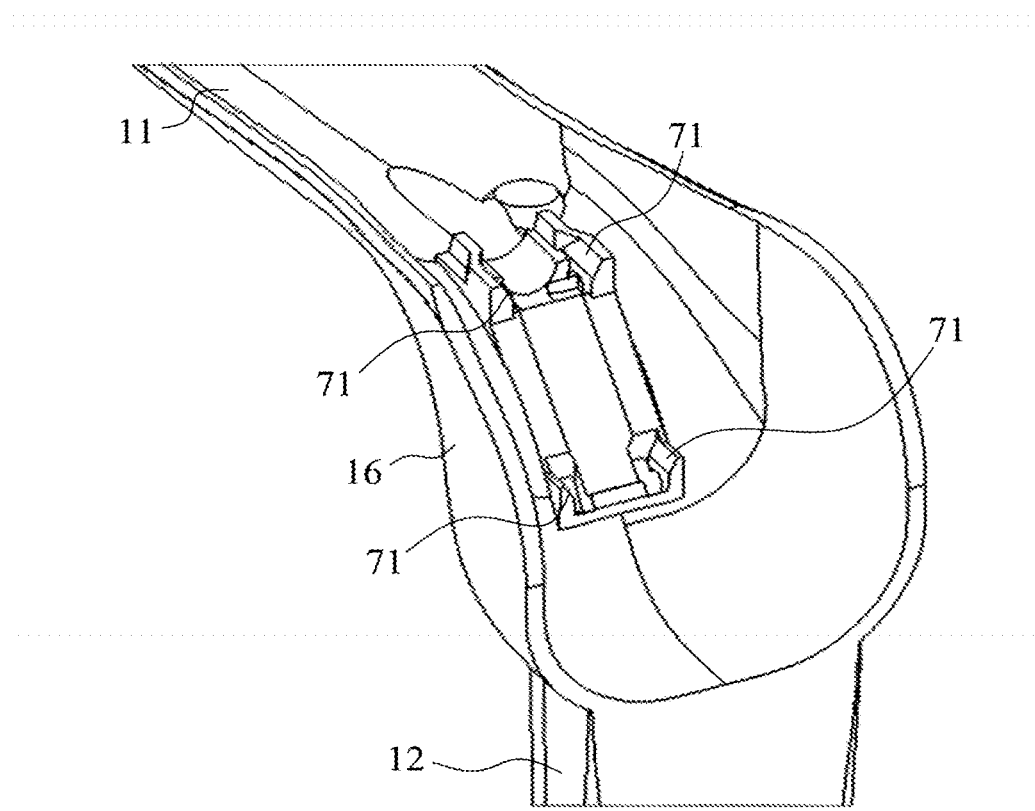
FIG. 7 is a partially enlarged view of the illuminated surgical retractor of FIG. 1 with the illumination assembly removed.
Figure 8:
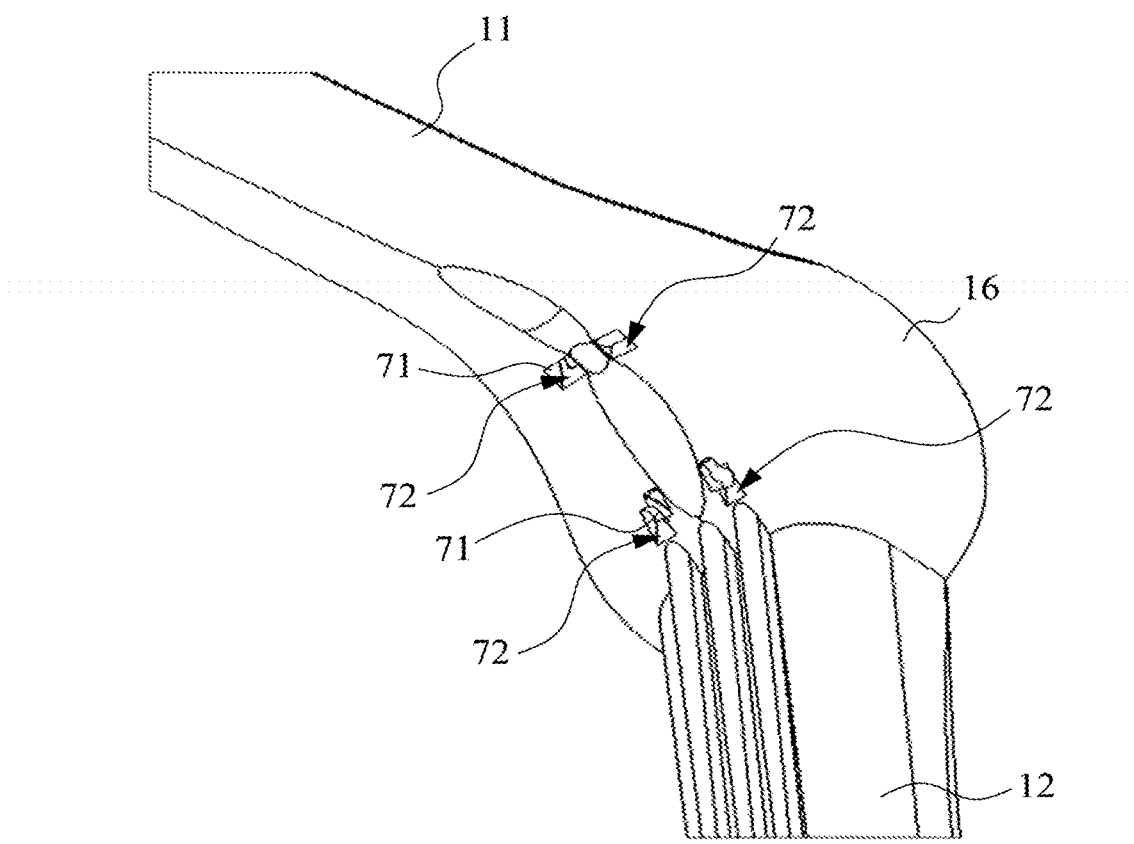
FIG. 8 is a partially enlarged view of the illuminated surgical retractor of FIG. 1 with the illumination assembly removed.

FIGS. 7-8 are partially enlarged views of the illuminated surgical retractor 10 of FIG. 1 with the illumination assembly 50 removed. As shown in FIGS. 7-8, the illuminated surgical retractor 10 further includes a plurality of acceptance slots 71 and an acceptance cavity 72. The acceptance slots 71 are located vertically, horizontally, or at an angle with the curved section 16, and are configured for accepting the retaining tabs 52. The acceptance slots 71 are in communication with the acceptance cavity 72 (shown in FIG. 8). When the retaining tabs 52 are inserted fully into the acceptance slots 71, the retaining tabs 52 arrive at the acceptance cavity 72. The acceptance cavity 72 is arranged to remove compression on the retaining tabs 52 and will inhibit the removal of the retaining tab 52 from the acceptance cavity 72. In this embodiment, the acceptance cavity 72 is recessed into the retractor component 15 such that the retaining tabs 52 will not protrude from the surface of retractor component 15. The lack of any protrusion allows for a smooth surface of the blade 11 and the handle 12, and an angled area between the blade 11 and the handle 12 prevents tissue irritation during medical procedures.

The retaining tabs 52, the retaining legs 53, the acceptance slots 71, and the acceptance cavity 72 allow novel flexibility in the creation of injection molds for the retractor component 15. In this embodiment, the injections slots are vertical, as required for molds that are designed to be released vertically. One having ordinary skill in the art of injection molding will recognize that the shape of the retractor component 15 requires molds that release vertically.

Other embodiments of the retractor component 15 may contain shapes that require horizontal mold releases and thus will have horizontal acceptance slots and cavities. The non-directional shape of the retaining tab 52 allows the illumination assembly 50 to be utilized with either vertically released molds or horizontally released molds. The use of a common illumination assembly 50 for a wide variety of retractor shapes dramatically lowers the cost of the illuminated surgical retractor 10.

The embodiments described herein provide a novel, low cost illumination assembly 50 attached in a unique location of the illuminated surgical retractor 10 which eliminates the expensive electrical and/or optical interconnection between the handle 12 and the blade 11 of previous retractors.

The illumination assembly 50 is attached to the illuminated surgical retractor 10 in a novel way so as to be compatible with a wide assortment of retractor shapes which can be molded vertically or horizontally. The chemical capacity of the batteries 62 is sufficient for only a single use and the illuminated surgical retractor is discarded after the single use. The intrinsic low cost of these embodiments makes the illuminated surgical retractor 10 economically attractive, and eliminates the inefficiency and expense of cleaning and re-sterilization. Recent evidence is emerging that procedures for cleaning and sterilization are often flawed in practice, resulting in possible cross contamination of patients. The embodiments described herein completely eliminate the risk of cross contamination by ensuring that each of the illuminated surgical retractor 10 is only used once.

In one or more embodiments, the blade, the handle and the curved section (referred to herein collectively as "the body") are integrally molded. In at least one exemplary embodiment, the material of which the body is formed is a strong, rigid, lightweight plastic (e.g., a polymer). One example of a suitable plastic is a glass-fiber reinforced polyarylamide compound that provides high strength and rigidity, surface gloss, and creep resistance. An exemplary embodiment uses a 50% glass-fiber reinforced polyarylamide compound, but those skilled in the art will understand that other percentages may be used without departing from the spirit and scope of the claimed invention.

Polyarylamides are thermoplastic crystalline polymers of aromatic diamines and aromatic dicarboxylic anhydrides having good heat, fire, and chemical resistance, property retention at high temperatures, dielectric and mechanical properties, and stiffness but low light resistance and processability. Those skilled in the art will understand that other plastics with suitable strength and rigidity also may be used.

In one or more embodiments, the body is made of a plastic (such as glass-fiber reinforced polyarylamide) having properties of at least one of radiolucence and nonconductivity. As used herein, "radiolucence" means high transparency to radiation, so that the device may be used when taking, for example, x-ray images. "Nonconductive," as used herein, means essentially dielectric.

Figure 9:
FIG. 9 is a fluoroscopy image illustrating the radiolucency of an embodiment.

An advantage of radiolucence is that the device may be used when taking X-ray images, without obscuring essential structures, as shown in FIG. 9. The "OBP" in FIG. 9 resulted from metal lettering placed below the blades of an embodiment to show the radiolucency. The much darker image on the left is of a stainless steel comparison blade, which shows up as black due to its opacity with respect to X-rays.

Embodiments described herein may provide light to the tip of the retractor and still remain highly (as much as 99%) radiolucent. Prior art devices have, for example, fiber optic cables that obstruct the view when X-ray images are taken, even when the devices are constructed of plastic. Metal devices are, of course, not radiolucent at all.

This radiolucent property means that retractors described herein may not need to be removed prior to the use of imaging techniques in surgical procedures. This can expedite the conduct of a procedure needing anatomic identification and/or device localization.

An advantage of nonconductivity is that it provides improved safety to patients—in contrast to metal retractors. Currents as low as 0.001 A may be felt by a patient, and larger currents may damage the patient. Embodiments described herein limit currents to less than $10^{-6}$ A, and thus greatly reduce electrical hazards.

For example, electro-cautery is used extensively in surgical tissue dissection. The use of metal retractors exposes the operating surgeon and the patient to the risk of retracted tissue damage due to destructive cautery current being conducted inadvertently. Retractors are often used to displace and retract delicate cautery sensitive tissues such small or large bowel (colon), lung, or major blood vessels. Cautery injury to these tissues can create major complications. In addition, retractors are often used to develop surgical tissue pockets in breast and pacemaker surgery. Use of a non-electrical conducting material, such as is described herein with respect to certain embodiments, prevents any stray electrical energy injury to the retracted tissues. Patient safety is thus enhanced.

As those skilled in the art will understand, strength is a function of both the material and the design. Designs using weaker material than is described herein need to be thicker and more rounded. Both of these traits will decrease the favorability of a retractor, which should not block visibility of the body cavity.

Flexural Strength represents the limit before a material will break under stress. Flexural modulus is the tendency of the material to bend under stress. Both of these parameters are critical to retractor design and resulting performance. First, a retractor blade must be thin enough to not interfere with the medical procedure for which it is used. Very thick blades will tend to fill the hole in the body that the physician needs to work in. An optimal design will have a blade thin enough to allow space for the physician to work. Typically metal blades are used because of their high Flexural modulus. They have unlimited flexural strength, because they bend rather than break. Metal blades as thin as 0.5-2 mm are readily available and this thickness is small enough to not interfere with the physician's work space in a wound or operating cavity. Stainless steel metal can have a flexural modulus of 180 Gpa which will inhibit blade deformation of more than 10 mm under 15 lbs of tip pressure for most retractor designs.

Plastic injection molded blades require a thicker blade because they have a lower Flexural Modulus. Blade strength will increase as the cube of the blade thickness, but blade thicknesses larger than 2 mm are not desirable in most physician applications. Typical plastic materials, such as those shown in Table 1 below, have a Flexural Modulus of just a few Gpa and a Flexural Strength of less than 200 Mpa. These lower value parameters result in retractor blades that deform more than 10 mm under use, and are likely to break with less than 30 lbs of force placed on the tip of an average length retractor blade (50-150 mm long).

Retractor blades that deform significantly during use increase the physician's difficulty in retracting the tissue during a medical procedure. Retractor blades that break with less than 30 lbs of force can create a hazard to the patient since a broken blade, or pieces of a broken blade, may fall into the patient and create damage. Retractor blades made from the plastics listed in the following table will typically bend more than 20 mm under 10 lbs of tip force, and will break at 15 lbs (or even less) of tip force.

TABLE 1

TYPICAL FLEXURAL STRENGTH AND FLEXURAL MODULUS OF POLYMERS

| POLYMER TYPE | FLEXURAL STRENGTH (MPa) | FLEXURAL STRENGTH (MPa) |
| --- | --- | --- |
| Polyamide-Imide | 175 | 5 |
| Polycarbonate | 90 | 2.3 |
| Polyethylene, MDPE | 40 | 0.7 |
| Polyethylene Terephthalate (PET) | 80 | 1 |

Figure 10:
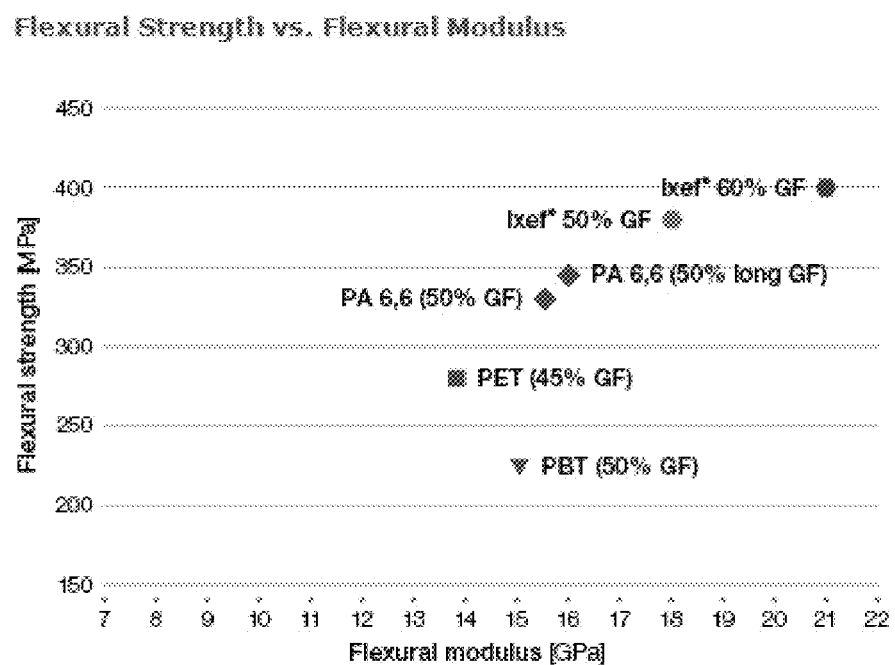
FIG. 10 illustrates flexural strength and flexural modulus for a variety of plastics.

To increase the Flexural modulus and Flexural strength of plastic, in an embodiment, glass fiber is added to the plastic material. FIG. 10 shows a variety of plastics with various percentages of glass fiber added.

It can be seen from the above that the addition of glass fiber can increase the Flexural Strength of certain plastics to 300 Mpa or above, and increase the Flexural Modulus to 16 Gpa or above. In an exemplary embodiment, a certain type of plastic, polyacrylamide is infused with glass fiber to create a flexural strength of over 375 Gpa and a Flexural modulus of over 17 Gpa.

Plastics with these properties have the ability to create retractor blades of approximately 2 mm thickness that withstand over 30 lbs of tip force without breaking and deform less than 10 mm under 15 lbs of force. Additionally, the glass fiber in this material will "glassify" at the surface leaving a very smooth "metal like" finish which is highly desirable in retractor applications.

The glass fiber in the material also will decrease the likelihood of sharp shards of material being created during an overstress and breakage event. This tendency to create dull edges upon breakage decreases the likelihood that a patient will experience damage if the retractor is overstressed and ultimately broken.

Additionally, the way in which a material breaks can be important in medical applications. The breakage characteristics of a material are often measured by Impact Strength. Materials with low impact strength (10-20 J/M) can break under stress into large numbers of sharp shards which can pose a hazard to a patient if material failure occurs during a medical procedure. Sharp shards can cut patient tissue and large numbers of these shards can make it difficult or impossible to remove the broken material from the patient.

Materials (such as glass fiber reinforced polyarylamide) used in certain embodiments described herein have a high impact strength (>100 J/M) and will fail with very few fractured component edges (and the resulting edges will be blunt). This breakage characteristic minimizes potential hazard to a patient during product overstress that results in material breakage.

In summary, when compared with the prior art, one or more embodiments described herein have at least the following advantages:

(1) The non-directional shape of the retaining tab allows the illumination assembly to be utilized with either vertically released molds or horizontally released molds. This use of a common illumination assembly for a wide variety of retractor shapes dramatically lowers the cost of the illuminated surgical retractor.

(2) The chemical capacity of the batteries is sufficient for only a single use and the illuminated surgical retractor is discarded after the single use. The intrinsic low cost of these embodiments makes the illuminated surgical retractor economically attractive, and eliminates the inefficiency and expense of cleaning and re-sterilization. Moreover, using an LED light source as opposed to halogen is advantageous since halogen bulbs get very hot and often burn the skin surrounding the surgical pocket in which a surgeon is working.

(3) The materials used to construct the retractor provide significant safety and advantages over prior art retractors, including, but not limited to, at least one of the following: (a) no danger from insufficient re-sterilization; (b) nonconductivity; (c) radiolucence; (d) high flexural strength and modulus; and (e) high impact strength.

Although the invention has been described in considerable detail herein with reference to certain embodiments thereof, other embodiments are possible. Therefore, the spirit and scope of the appended claims should not be limited to any non-claimed details of the embodiments contained herein.

It will be apparent to the person having ordinary skill in the art that various modifications and variations can be made to the structure of the embodiments described herein without departing from the scope or spirit of the claimed invention. In view of the foregoing, it is intended that the claimed inventions cover modifications and variations of the embodiments described herein provided they fall within the scope of the following claims.

I claim:

1. An illuminated surgical retractor, comprising:
a blade having a top surface and a bottom surface;
a handle extending at an angle from a proximal end of the blade;
a curved section connecting the handle to the blade; and
an illumination assembly comprising at least one light source, at least one battery and an activation device comprising one of a switch and a removable dielectric tab for energizing the light source, and the illumination assembly being non-releasably attached to the retractor;
wherein the blade, handle, and curved section are molded from a glass-fiber reinforced polymer having a flexural strength of at least 300 Mpa; and
wherein the blade, being molded from the glass-fiber reinforced polymer, deforms less than 10 mm under 15 lbs of force applied thereto.

2. The illuminated surgical retractor of claim 1, wherein the polymer is a 50 wt % glass-fiber reinforced polymer.

3. The illuminated surgical retractor of claim 1, wherein the polymer is a polyarylamide compound.

4. The illuminated surgical retractor of claim 1, wherein the polymer is a thermoplastic crystalline polymer.

5. The illuminated surgical retractor of claim 4, wherein the polymer is a thermoplastic crystalline polymer of aromatic diamines and aromatic dicarboxylic anhydrides.

6. The illuminated surgical retractor of claim 1, wherein the polymer is a glass-fiber reinforced polyarylamide.

7. The illuminated surgical retractor of claim 6, wherein the polymer is at least 50 wt % glass-fiber reinforced.

8. The illuminated surgical retractor of claim 1, wherein the polymer has a flexural modulus of at least 17 Gpa.

9. The illuminated surgical retractor of claim 1, wherein the polymer has a flexural strength of at least 375 Mpa.

10. The illuminated surgical retractor of claim 1, wherein the polymer has an impact strength of at least 100 J/M.

11. The illuminated surgical retractor of claim 1, wherein the illumination assembly is non-releasably attached to the curved section.

12. The mated surgical retractor of claim 1, wherein a proximal tip of the blade withstands over 30 lbs of force applied thereto.

13. The illuminated surgical retractor of claim 1, wherein the polymer has a flexural modulus of at least 16 Gpa.

14. The illuminated surgical retractor of claim 1, wherein he blade has a thickness of approximately 2 mm.

15. An illuminated surgical retractor, comprising:
a blade having a top surface and a bottom surface;
a handle extending at an angle from a proximal end of the blade;
a curved section connecting the handle to the blade; and
an illumination assembly comprising at least one light source, at least one battery and an activation device comprising one of a switch and a removable dielectric tab for energizing the light source, and the illumination assembly being non-releasably attached to the retractor;
wherein the blade handle, and curved section are molded from a polymer, said polymer being a low conductivity polymer and a radiolucent polymer;
wherein said polymer has a flexural strength of at leas 300 Mpa; and
wherein the blade, being molded from the polymer, deforms less than 10 mm under 15 lbs of force applied thereto.

16. The illuminated surgical retractor of claim 15, wherein the polymer has a flexural modulus of at least 16 Gpa.

17. The illuminated surgical retractor of claim 15, wherein the polymer is a 50 wt % glass-fiber reinforced polymer.

18. The illuminated surgical retractor of claim 15, wherein the polymer is a polyarylamide compound.

19. The illuminated surgical retractor of claim 15, wherein the polymer is a thermoplastic crystalline polymer.

20. The illuminated surgical retractor of claim 19, wherein the polymer is a thermoplastic crystalline polymer of aromatic diamines and aromatic dicarboxylic anhydrides.

21. The illuminated surgical retractor of claim 15, wherein the polymer comprises a non-conductive material that limits currents to less than $10^{-6}$ A.

22. The illuminated surgical retractor of claim 15, wherein the illumination assembly is non-releasably attached to the curved section.

23. The illuminated surgical retractor of claim 15, wherein the blade has a thickness of approximately 2 mm.

24. An illuminated surgical retractor, comprising:
a blade having a top surface and a bottom surface;
a handle extending at an angle from a proximal end of the blade;
a curved section connecting the handle to the blade; and
an illumination assembly comprising at least one light source, at least one battery and an activation device comprising one of a switch and a removable dielectric tab for energizing the light source, and the illumination assembly being non releasably attached to the retractor;
wherein the blade, handle, and curved section are molded from a low conductivity polymer; and
wherein the polymer comprises a non-conductive material that limits currents to less than $10^{-6}$ A.

25. The illuminated surgical retractor of claim 24, wherein the blade, being molded from the polymer, deforms less than 10 mm under 15 lbs of force applied thereto.

26. The illuminated surgical retractor of claim 24, wherein a proximal tip of the blade withstands over 30 lbs of force applied thereto.

* * * * *